US 7,560,251 B2

(12) United States Patent
Wang et al.

(10) Patent No.: US 7,560,251 B2
(45) Date of Patent: *Jul. 14, 2009

(54) **MEDIA FOR *CLOSTRIDIUM* BACTERIUM**

(75) Inventors: Ping Wang, Irvine, CA (US); Stephen Donovan, Capistrano Beach, CA (US)

(73) Assignee: Allgergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/609,449

(22) Filed: Dec. 12, 2006

(65) Prior Publication Data

US 2007/0111288 A1 May 17, 2007

Related U.S. Application Data

(60) Division of application No. 11/072,050, filed on Mar. 3, 2005, now Pat. No. 7,160,699, which is a continuation-in-part of application No. 10/672,876, filed on Sep. 25, 2003, now Pat. No. 7,148,041.

(51) Int. Cl.
*C12N 1/20* (2006.01)
*C07K 14/33* (2006.01)

(52) U.S. Cl. ............... 435/71.1; 435/252.7; 435/253.6; 424/236.1; 424/239.1

(58) Field of Classification Search ............... 435/71.1, 435/252.7, 253.6; 424/842, 236.1, 239.1
See application file for complete search history.

(56) References Cited

U.S. PATENT DOCUMENTS

| 4,401,683 | A | 8/1983 | Thompson | |
|---|---|---|---|---|
| 6,558,926 | B1 | 5/2003 | Demain et al. | 435/71.1 |
| 6,818,409 | B2 | 11/2004 | Oguma | |
| 7,445,914 | B2 * | 11/2008 | Donovan | 435/71.1 |
| 2003/0118598 | A1 | 6/2003 | Hunt et al. | |
| 2004/0235139 | A1 | 11/2004 | Demain et al. | 435/252.7 |
| 2005/0069562 | A1 | 3/2005 | Donovan | 424/239.1 |
| 2005/0238668 | A1 | 10/2005 | Wang et al. | 424/239.1 |
| 2005/0238669 | A1 | 10/2005 | Xiang et al. | 424/239.1 |

FOREIGN PATENT DOCUMENTS

| WO | WO 94/09115 | 4/1994 |
|---|---|---|
| WO | WO 96/05222 | 2/1996 |
| WO | WO 98/54296 | 12/1998 |
| WO | WO 01/05997 A2 | 1/2001 |
| WO | WO 01/05997 A3 | 1/2001 |
| WO | WO 01/36655 | 5/2001 |
| WO | WO 01/58472 | 8/2001 |
| WO | WO 2005/035749 A2 | 4/2005 |

OTHER PUBLICATIONS

Bonventre, P.F., et al., *Physiology of toxin production by Clostridium botulinum types A and B*, Appl. Microbiol., 1957, vol. 7, pp. 372-374.
Chen, F., et al., *Biophysical characterization of the stability of the 150-kilodalton botulinum toxin, complex species*, Infect Immun, Jun. 1998, 66(6), pp. 2420-2425.
Eds: Coligan, John E., et al., *Strategies of Protein Purification and Characterization*, Chpt. 1, and *Peptidases*, Chpt. 21, in Current Protocols in Protein Science, Front Matter, 2003.
Henan, C.N., et al., Lehensm.-Wiss. U.-Technol., 35 (2002), pp. 171-176.
Holdeman, L., et al., *A study of the nutritional requirements and toxin production of Clostridium botulinum type F*, Canadian Journal of Microbiology, vol. 11, 1965, pp. 1009-1019.
Johnson, E., et al., *Clostridium botulinum and its neurotoxins: a metabolic and cellular perspective*, Toxicon, 39 (2001), pp. 1703-1722.
Karasawa, T., et al., *A defined growth medium for Clostridium difficle*, Microbiology (1995), 141, pp. 371-375.
Kohl., A., et al., *Comparison of the effect of botulinum toxin A (BOTOX®) with the highly-purified neurotoxin (NT201) in the extensor digitorum brevis muscle test*, Mov. Disord, 2000, 15(Suppl 3):165.
Bedu-Addo, F., et al. "Use of Biophysical characterization in preformulation development of a heavy-chain fragment of botulinum serotype B: Evaluation of suitable purification process conditions." *Pharmaceutical Research* 21.8 (2004): 1353-1361.
Byrne, M., et al. "Purification, potency, and efficacy of the botulinum type A binding domain from *Pichia pastoris* as a recombinant vaccine candidate," *Infection and Immunity* 66.10 (1998): 4817-4822.

(Continued)

*Primary Examiner*—Chih-Min Kam
(74) *Attorney, Agent, or Firm*—Claude L. Nassif; Stephen Donovan; Debra D. Condino

(57) ABSTRACT

Animal product free (APF) media and processes for the culture and fermentation of botulinum toxin producing *Clostridium botulinum* bacteria. The botulinum toxin obtained can be used for formulating and compounding botulinum toxin pharmaceutical compositions. The APF media can contain significantly reduced levels of meat or dairy by-products and use non-animal based products instead of the animal-derived products. Preferably, the APF media used are substantially free or free of animal derived products.

14 Claims, 3 Drawing Sheets

OTHER PUBLICATIONS

Figure 1:
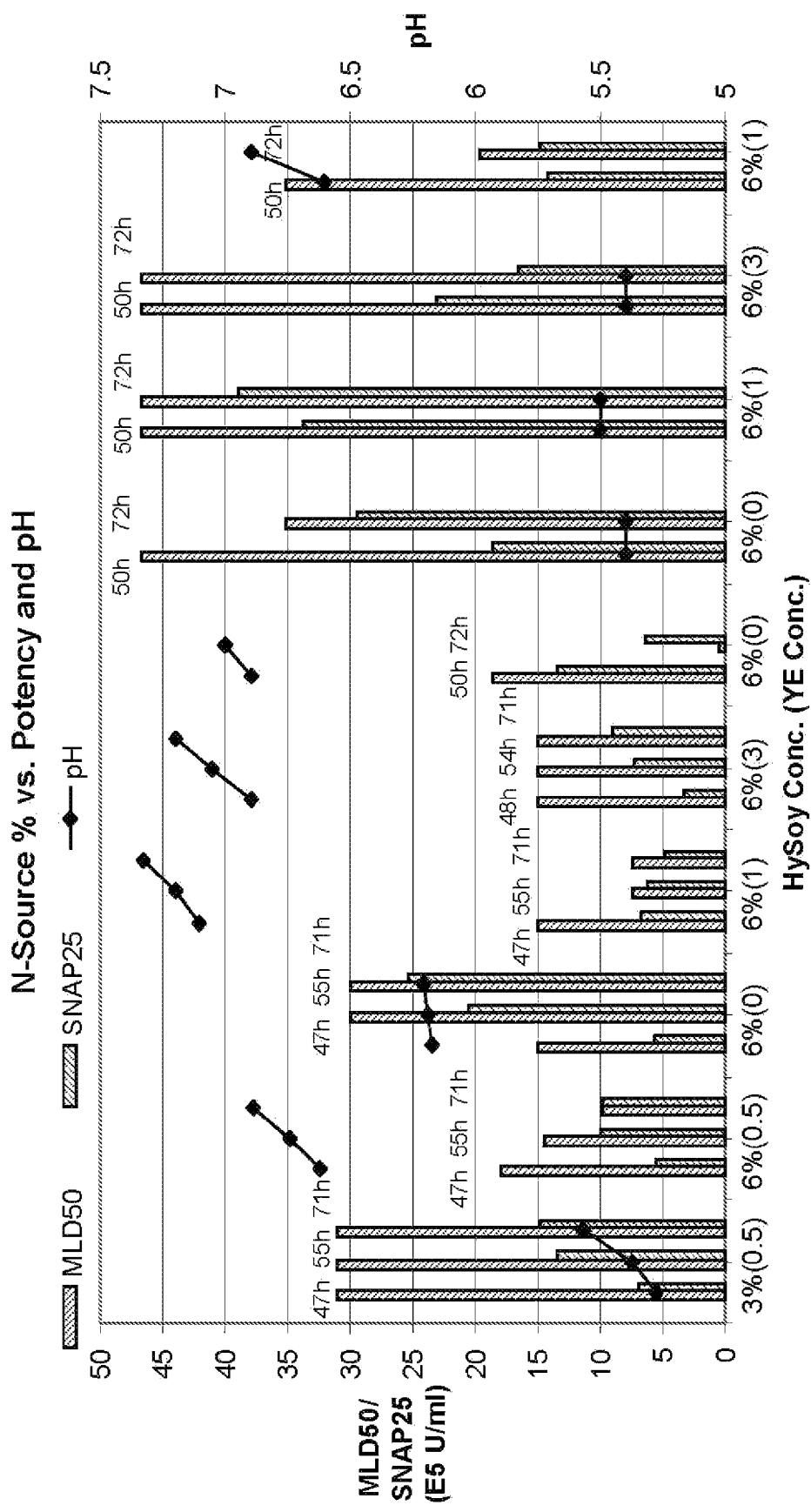

Gessler, F., et al. "Production and purification of *Clostridium botulinum* type C and D neurotoxin." *FEMS Immunology and Medical Microbiology* 24 (1999): 361-367.

Gimenez, J., et al. "Simplified purification method for *Clostridium botulinum* type E toxin." *Applied and Environmental Microbiology* 53.12 (Dec. 1987): 2827-2830.

Huhtanen, C.N. "Some observations on a perigo-type inhibition of *Clostridium botulinum* in a simplified medium." *Journal of Milk and Food Technology* 38.12 (Dec. 1975): 761-763.

Johnson, S., et al. "Scale-up of the fermentation and purification of the recombinant heavy chain fragment C of *botulinum* neurotoxin serotype F, expressed in *Pichia pastoris*." *Protein Expression and Purification* 32 (2003): 1-9.

Kozaki, S., et al. "Immunological characterization of papain-induced fragments of *Clostridium botulinum* type A neurotoxin and interaction of the fragments with brain synaptosomes." *Infection and Immunity* 57.9 (1989): 2634-2639.

Prabakaran, S., et al. "*Botulinum* neurotoxin types B and E: Purification, limited proteolysis by endoproteinase Glu-C and Pepsin, and comparison of their indentified cleaved sites relative to the three-dimensional structure of type A neurotoxin." *Toxicon* 39 (2001): 1515-1531.

Schantz, E.J., et al., Lewis, G.E. "Use of Chrystalline type A *botulinum* toxin in medical research." *Biomedical Aspects of Botulism*, Academic Press, Inc., George E. Lewis, Jr., Ed., 1981: 143-150.

Siegel, L.S. "Toxin production by *Clostridium botulinum* type A under various fermentation conditions." *Applied and Environmental Microbiology* Oct. 1979: 606-611.

Tse, et al. *European Journal of Ciochemistry* 122 (1982): 493-500.

Weatherly, G., et al. "Initial purification of recombinant *botulinum* neurotoxin fragments for pharmaceutical production using hydrophobic charge induction chromatography." *Journal of Chromatography A* 952 (2002): 99-110.

Young-Perkins, et al. *Journal of Food Science* 52 (1987): 1084-1088.

Lewis, K.H., et al., *Practical media and control measures for highly toxic cultures of Clostridium botulinum type A*, Production of Botulinum Toxin, pp. 213-230, 1947.

Li, Y., et al., *Expression and characterization of the heavy chain of tetanus toxin: reconstitution of the fully-recombinant dichain protein in active form*, J. Biochem (Tokyo) Jun. 1999, 125(6), pp. 1200-1208.

Ljungdahl, L.G., et al., *Working with Anaerobic Bacteria*, Manual of Industrial Microbiology and Biotechnology, Chp. 8, 1986, pp. 84-96.

Miwa, Norinaga, et al., International Journal of Food Microbiology, 49 (1999), pp. 103-106.

Mueller, J.H., et al., *Variable factors influencing the product of tetanus toxin*, J. Bacteriol, 1954, 67:271-7.

Naumann, M., et al., *Botulinum toxin type A in the treatment of focal, axillary and palmar hyperhidrosis and other hyperhidrotic conditions*, Euro. J. Neurology, 1999:6(Suppl 4), pp. S111-S115.

Oxoid—Product CM0149—product description, pp. 1-2, 2004.

Ozutsumi, K., et al., *Rapid, simplified method for production and purification of tetanus toxin*, Applied and Environmental Microbiology, Apr. 1985, vol. 49, No. 4, pp. 939-943.

Porfirio, Z., et al., *Specific peptides of casein pancreatic digestion enhance the production of tetanus toxin*, J. of Applied Microbiology, 1997, 83, pp. 678-684.

Ragona, Rosario Marchese, et al., *Management of Parotid Sialocele with Botulinum Toxin*, The Laryngoscope, 109, Aug. 1999, pp. 1344-1346.

Schantz, E.J., et al., *Preparation and Characterization of Botulinum Toxin Type A for Human Treatment*, Jankovic J, eds., In: Therapy with Botulinum Toxin, 1994, pp. 41-49.

Schantz, E.J., et al., *Properties and use of botulinum toxin and other microbial neurotoxins in medicine*, Microbiological Reviews, Mar. 1992, pp. 80-99.

Schiefer-Ullrich, H., et al., *Comparative studies on physiology and taxonomy of obligatory purinolytic clostridia*, Arch Microbiol, 1984, 138, pp. 345-353.

Siegel, L.S., *Fermentation kinetics of botulinum toxin production (types A, B, and E)*, Biomedical aspects of botulism, New York: Academic Press 1981, pp. 121-128.

Whitmer, M.E., et al., *Development of improved defined media for Clostridium botulinum serotypes A, B and E*, Applied and Environmental Microbiology, Mar. 1988, vol. 54, No. 3, pp. 753-759.

\* cited by examiner

MEDIA FOR *CLOSTRIDIUM* BACTERIUM

CROSS REFERENCE

This application is a divisional of U.S. application Ser. No. 11/072,050, filed Mar. 3, 2005, now U.S. Pat. No. 7,160,699, which is a continuation in part of U.S. application Ser. No. 10/672,876, filed Sep. 25, 2003, now U.S. Pat. No. 7,148,041, the entire contents of which applications are incorporated herein by reference.

BACKGROUND

The present invention relates to media and processes for obtaining biologically active botulinum toxin. In particular, the present invention relates to substantially animal product free, media, culture and anaerobic fermentation processes of an organism, such as a *Clostridium botulinum* bacterium, for obtaining abundant, biologically active botulinum toxin.

A pharmaceutical composition suitable for administration to a human or animal for a therapeutic, diagnostic, research or cosmetic purpose can comprise an active ingredient. The pharmaceutical composition can also include one or more excipients, buffers, carriers, stabilizers, preservatives and/or bulking agents. The active ingredient in a pharmaceutical composition can be a biologic such as a botulinum toxin. The botulinum toxin active ingredient used to make a botulinum toxin pharmaceutical composition can be obtained through a multi step culturing, fermentation and compounding process which makes use of one or more animal derived products (such as meat broth and casein ingredients in one or more of the culture and fermentation media used to obtain a bulk botulinum toxin, and a blood fraction or blood derivative excipient in the final compounded botulinum toxin pharmaceutical composition). Administration to a patient of a pharmaceutical composition wherein the active ingredient biologic is obtained through a process which makes use of animal derived products can subject the patient to a potential risk of receiving various pathogens or infectious agents. For example, prions may be present in a pharmaceutical composition. A prion is a proteinaceous infectious particle which is hypothesized to arise as an abnormal conformational isoform from the same nucleic acid sequence which makes the normal protein. It has been further hypothesized that infectivity resides in a "recruitment reaction" of the normal isoform protein to the prion protein isoform at a post translational level. Apparently the normal endogenous cellular protein is induced to misfold into a pathogenic prion conformation.

Creutzfeldt-Jacob disease is a rare neurodegenerative disorder of human transmissible spongiform encephalopathy where the transmissible agent is apparently an abnormal isoform of a prion protein. An individual with Creutzfeldt-Jacob disease can deteriorate from apparent perfect health to akinetic mutism within six months. Thus, a potential risk may exist of acquiring a prion mediated disease, such as Creutzfeldt-Jacob disease, from the administration of a pharmaceutical composition which contains a biologic, such as a botulinum toxin, obtained or compounded using animal derived products.

Botulinum Toxin

The genus *Clostridium* has more than one hundred and twenty seven species, grouped by morphology and function. The anaerobic, gram positive bacterium *Clostridium botulinum* produces a potent polypeptide neurotoxin, botulinum toxin, which causes a neuroparalytic illness in humans and animals known as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. On a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63-84 (chapter 4) of *Natural Toxins II*, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). BOTOX® is the trademark of a botulinum toxin type A purified neurotoxin complex available commercially from Allergan, Inc., of Irvine, Calif. One unit (U) of botulinum toxin is defined as the $LD_{50}$ upon intraperitoneal injection into female Swiss Webster mice weighing about 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of e.g. neuromuscular disorders characterized by hyperactive skeletal muscles. Botulinum toxin type A has been approved by the U.S. Food and Drug Administration for the treatment of essential blepharospasm, strabismus and hemifacial spasm in patients over the age of twelve, for the treatment of cervical dystonia and for the treatment of glabellar line (facial) wrinkles. The FDA has also approved a botulinum toxin type B for the treatment of cervical dystonia. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and botulinum toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Botulinum neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with one or more associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. Thus, a botulinum toxin complex can comprise a botulinum toxin molecule (the neurotoxic component) and one or more non toxic, haemagluttinin proteins and/or non toxin, non haemagluttinin proteins (the later can be referred to as NTNH proteins) These two types of non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. or by subjecting the complex to a separation process, such as column chromatography, in a suitable buffer at a pH of about 7-8. The botulinum toxin protein has a marked instability upon removal of the hemagglutinin protein.

All the botulinum toxin serotypes are made by native Clostridium botulinum bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by non-proteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin for use in a pharmaceutical composition can be obtained by anaerobic fermentation of Clostridium botulinum using a modified version of the well known Schantz process (see e.g. Schantz E. J., et al., *Properties and use of botulinum toxin and other microbial neurotoxins in medicine*, Microbiol Rev 1992 March; 56(1):80-99; Schantz E. J., et al., *Preparation and characterization of botulinum toxin type A for human treatment*, chapter 3 in Jankovic J, ed. Neurological Disease and Therapy. Therapy with botulinum toxin (1994), New York, Marcel Dekker; 1994, pages 41-49, and; Schantz E. J., et al., *Use of crystalline type A botulinum toxin in medical research*, in: Lewis G E Jr, ed. *Biomedical Aspects of Botulism* (1981) New York, Academic Press, pages 143-50.).

Botulinum toxins (the 150 kilodalton molecule) and botulinum toxin complexes (300 kDa to 900 kDa) can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A purified neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin hemagglutinin complex with human serum albumin and lactose in the botulinum toxin pharmaceutical composition), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Solstice Neurosciences (formerly available from Elan Corporation, Dublin, Ireland) of San Diego, Calif.

The success of botulinum toxin type A to treat a variety of clinical conditions has led to interest in other botulinum toxin serotypes. Thus, at least botulinum toxins types, A, B, E and F have been used clinically in humans. Additionally, pure (approx 150 kDa) botulinum toxin has been used to treat humans. See e.g. Kohl A., et al., *Comparison of the effect of botulinum toxin A (Botox®) with the highly-purified neurotoxin (NT 201) in the extensor digitorum brevis muscle test*, Mov Disord 2000; 15(Suppl 3):165. Hence, a botulinum toxin pharmaceutical composition can be prepared using a pure (approx 150 kDa) botulinum toxin, as opposed to use of a botulinum toxin complex.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

It has been reported that a botulinum toxin has been used in various clinical settings, including as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
 (a) flexor digitorum profundus: 7.5 U to 30 U
 (b) flexor digitorum sublimus: 7.5 U to 30 U
 (c) flexor carpi ulnaris: 10 U to 40 U
 (d) flexor carpi radialis: 15 U to 60 U
 (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session. (7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999), and in some circumstances for as long as 27 months. *The Laryngoscope* 109:1344-1346:1999. However, the usual duration of an intramuscular injection of Botox® is typically about 3 to 4 months.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine casein and yeast extract. The botulinum toxin type A complex is purified from the culture solution by a series of acid or acid and ethanol precipitations to a crystalline complex consisting of the active high molecular weight toxin protein and an associated hemagglutinin protein. The crystalline complex is redissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. Reconstituted BOTOX® can be stored in a refrigerator (2° to 8° C.) and is a clear, colorless liquid and free of particulate matter. There are reports of reconstituted BOTOX® retaining its potency for up to thirty days. See e.g. Guttman C., *Botox retains its efficacy for blepharospasm treatment after freezing and storage, New York investigators find*, EuroTimes 2000 November/December; 5(8):16. The vacuum-dried product is stored in a freezer at or below −5° C.

In general, four physiologic groups of *C. botulinum* are recognized (I, II, III, IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce botulinum neurotoxins.

The physiologic groups of *Clostridium botulinum* types are listed in Table I.

TABLE I

Physiologic Groups of *Clostridium botulinum*

| Group | Toxin Sero-Type | Biochemistry | Milk Digest | Glucose Fermentation | Lipase | Phages & Plasmids | Phenotypically Related *Clostridium* (nontoxigenic) |
|---|---|---|---|---|---|---|---|
| I | A, B, F | proteolytic saccharolytic | + | + | + | + | *C. sporogenes* |
| II | B, E, F | nonproteolytic saccharolytic psychotrophic | − | + | + | + | |
| III | C, D | Nonproteolytic saccharolytic | ± | + | + | + | *C. novyi* |
| IV | G | proteolytic nonsaccharolytic | + | − | − | − | *C. subterminale* |

These toxin types may be produced by selection from the appropriate physiologic group of *Clostridium botulinum* organisms. The organisms designated as Group I are usually referred to as proteolytic and produce botulinum toxins of types A, B and F. The organisms designated as Group II are saccharolytic and produce botulinum toxins of types B, E and F. The organisms designated as Group III produce only botulinum toxin types C and D and are distinguished from organisms of Groups I and II by the production of significant amounts of propionic acid. Group IV organisms produce only neurotoxin of type G.

It is known to obtain a tetanus toxin using specific media substantially free of animal products. See e.g. U.S. Pat. No. 6,558,926. But notably, even the "animal product free" media disclosed by this patent uses Bacto-peptone, a meat digest. Significantly, production of tetanus toxin by *Clostridium tetani* vs. production of a botulinum toxin by a *Clostridium botulinum* bacterium entails different growth, media and fermentation parameters and considerations. See e.g. Johnson, E. A., et al., *Clostridium botulinum and its neurotoxins: a metabolic and cellular perspective*, Toxicon 39 (2001), 1703-1722.

What is needed therefore are media and processes which are free or substantially free of animal products, such as animal derived proteins, for obtaining or producing biologically active botulinum toxin.

SUMMARY

The present invention meet this need and provides media and processes which are free or substantially free of animal products, such as animal derived proteins, for obtaining or producing a biologically active botulinum toxin. The botulinum toxin obtained can be used to make botulinum toxin active ingredient pharmaceutical compositions.

Definitions

As used herein, the words or terms set forth below have the following definitions.

"About" means that the item, parameter or term so qualified encompasses a range of plus or minus ten percent above and below the value of the stated item, parameter or term.

"Administration" or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intracranial. intraperitoneal (i.p.) administration, topical (transdermal) and implantation (i.e. of a slow-release device such as polymeric implant or miniosmotic pump) routes of administration.

"Animal product free" or "substantially animal product free" encompasses, respectively, "animal protein free" or "substantially animal protein free" and means the absence or substantial absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal product free medium or process or a substantially animal product free medium or process within the scope of the present invention can include a botulinum toxin or a *Clostridial botulinum* bacterium. For example, an animal product free process or a substantially animal product free process means a process which is either substantially free or essentially free or entirely free of animal derived proteins, such as immunoglobulins, meat digest, meat by products and milk or dairy products or digests. Thus, an example of an animal product free process is a process (such as a bacterial culturing or bacterial fermentation process) which excludes meat and dairy products or meat or dairy by products.

"Botulinum toxin" means a neurotoxin produced by *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F and G. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention. "Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 90%, preferably more than 95%, and most preferably more than 99% of the non-botulinum toxin proteins and impurities removed. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum, Clostridium butyricum* or *Clostridium beratti*, as well as a Clostridial neurotoxin made recombinantly by a non-Clostridial species.

"Entirely free" (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Patient" means a human or non-human subject receiving medical or veterinary care. Accordingly, as disclosed herein, the compositions may be used in treating any animal, such as mammals.

"Pharmaceutical composition" means a formulation in which an active ingredient can be a botulinum toxin. The word "formulation" means that there is at least one additional ingredient (such as an albumin and/or sodium chloride) in the pharmaceutical composition besides a neurotoxin active ingredient. A pharmaceutical composition is therefore a formulation which is suitable for diagnostic, therapeutic or cosmetic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The active ingredient can be one of the botulinum toxin serotypes A, B, $C_1$, D, E, F or G or a botulinum toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use. Methods for formulating a botulinum toxin active ingredient pharmaceutical composition are disclosed in U.S. patent publication 2003 0118598 A1.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

The present invention provides media which comprise at least reduced levels of animal or dairy byproducts and are preferably substantially free of animal or dairy byproducts. "Animal or dairy byproducts" means any compound or combination of compounds which was produced in or by an animal (excluding a bacterial) cell, whether in vivo or in vitro. Preferred non-animal sources of media ingredients such as proteins, amino acids, and nitrogen, include vegetables, microbes (such as yeast) and synthetic compounds.

Our invention also provides methods for obtaining botulinum toxin using at least one medium that is substantially free of animal or dairy byproducts. For example, the botulinum toxin can be obtained by culturing *Clostridium botulinum* in a fermentation medium which is substantially free of animal products.

Our invention also encompasses, a botulinum toxin obtained by culturing *Clostridium botulinum* in a fermentation medium substantially free of animal products and which comprises vegetable derived products. Additionally, a botulinum toxin can be obtained by culturing *Clostridium botulinum* in a fermentation medium which is substantially free of animal products and which comprises some soy-based products.

In another preferred embodiment, a botulinum toxin can be obtained by culturing *Clostridium botulinum* in a fermentation medium substantially free of animal products and containing hydrolyzed soy, as a substitute for animal-derived products. Preferably, growth in a fermentation medium proceeds until at least cell lysis occurs. The source of *Clostridium botulinum* used for inoculation of the fermentation medium may be obtained from a seed medium containing *Clostridium botulinum*. Preferably, *Clostridium botulinum* grown in a seed medium and used as an inoculum for a fermentation medium is in its' exponential growth phase. The source of *Clostridium botulinum* used for inoculation of the seed medium may be obtained from a lyophilized culture. *Clostridium botulinum* can be lyophilized as a culture in animal milk or soy milk. Preferably the *Clostridium botulinum* is lyophilized as a culture in soy milk.

The present invention also provides a composition comprising a medium substantially free of animal-derived products for culturing *Clostridium botulinum*.

In one embodiment, the composition comprises a medium substantially free of animal-derived products while containing at least one product derived from a non-animal source, and also comprising a *Clostridium botulinum*.

In another embodiment, the composition comprises a medium substantially free of animal-derived products while containing at least one product derived from a vegetable, and also comprising a *Clostridium botulinum*. A further embodiment of the invention can be a composition which comprises a medium which is substantially free of animal-derived products while containing at least one product derived from soybeans, and also comprising a *Clostridium botulinum*.

The present invention includes a method for obtaining a biologically active Clostridial toxin (such as a botulinum neurotoxin in an APF medium) by: (1) providing a fermentation medium (the fermentation medium is at least substantially free of an animal derived product and comprises between about 4-8% by weight of a soy derivative); (2) fermenting a *Clostridium botulinum* bacterium in the fermentation medium under conditions which permit production of a botulinum toxin, and; (3) recovering a biologically active botulinum toxin from the fermentation medium. In this method, the fermentation medium can also include between about 0-3% by weight of a yeast extract and between about 0.5 to 5% by weight glucose. Preferably the fermentation medium includes about 1-2% by weight glucose. The fermentation step can be carried out a pH of between about 5.0 and 5.5, for between about 45 hours and about 75 hours, at a temperature between about 33° and 36° C. and in an anaerobic atmosphere.

This method for obtaining a biologically active Clostridial toxin can comprise the further two steps (prior to step (1) above of providing a fermentation medium) of (a) obtaining a culture medium that is substantially free of an animal derived product and comprises between about 4-8% by weight of a soy derivative and (b) culturing a *Clostridium botulinum* bacterium in the culture medium.

Significantly, step (3) in this method of recovering a biologically active botulinum toxin from the fermentation medium can be or include an APF purification process.

A detailed embodiment of this method for obtaining a biologically active botulinum toxin can comprise the steps of:
(a) obtaining a culture medium that is substantially free of an animal derived product and comprises between about 4-8% by weight of a soy derivative and culturing a *Clostridium botulinum* bacterium in the culture medium;
(b) providing a fermentation medium that is substantially free of an animal derived product and comprises
   (i) between about 4-8% by weight of a soy derivative,
   (ii) between about 0-3% by weight of a yeast extract,
   (iii) between about 1-2% by weight glucose,
(c) fermenting a *Clostridium botulinum* bacterium in the fermentation medium under conditions which permit production of a botulinum toxin, including;
   (i) carrying out the fermentation step at a pH of between about 5.0 and 5.5,
   (ii) carrying out the fermentation step for between about 45 hours and 75 hours,
   (iii) carrying out the fermentation step at a temperature between about 33° and 36° C.,
   (iv) carrying out the fermentation step in an anaerobic atmosphere, and;
(d) recovering a biologically active botulinum toxin from the fermentation medium, wherein the recovering step is an APF purification process.

The present invention also includes a medium for culturing or for fermenting a botulinum toxin wherein the medium is substantially free of an animal derived product and comprises a protein product derived from a vegetable. The medium can comprise between about 4-8% by weight of a soy derivative, between about 0-3% by weight of a yeast extract and between about 1-2% by weight glucose.

The present invention also encompasses a method for making a substantially animal product free pharmaceutical composition in which the active ingredient is a botulinum toxin, the method comprising the steps of: (a) obtaining a biologically active botulinum toxin by;
   (i) providing a fermentation medium that is substantially free of an animal derived product;
   (ii) culturing a *Clostridium botulinum* in the fermentation medium under conditions which permit production of a botulinum toxin, and;
   (iii) recovering a biologically active botulinum toxin from the fermentation medium, and:
(b) compounding the botulinum toxin with a suitable excipient, thereby making a substantially animal product free pharmaceutical composition in which the active ingredient is a botulinum toxin.

Additionally, the present invention also encompasses a method for obtaining a biologically active botulinum toxin by: (a) providing a fermentation medium that is substantially free of an animal derived product and comprises between about 4-8% by weight of a soy derivative; (b) fermenting a *Clostridium botulinum* bacterium in the fermentation medium, wherein the fermentation medium is maintained at a pH between pH 5.0 and 5.5, and; (c) recovering a biologically active botulinum toxin from the fermentation medium.

Finally, the present invention also encompasses an animal protein free medium for culturing and/or for fermenting a *Clostridium botulinum* bacterium toxin. Preferably, the medium is substantially free of an animal derived product and comprises between about 4-8% by weight of a soy derivative; between about 0-3% by weight of a yeast extract, and; between about 1-2% by weight glucose.

DRAWINGS

Aspects of the invention are explained or illustrated by the following drawings.

FIG. 1 entitled "N-Source (i.e. HySoy plus YE) % vs. Potency and pH" is a graph showing botulinum toxin activity as determined: (1) on the left side Y axis mouse lethal dose 50 (MLD 50) (blue bars), and; (2) on the left side Y axis SNAP 25 activity (red bars), of various APF media at the elapsed fermentation times shown at the top of the bars, for APF medium pH as shown on the right side Y axis the pH, for APF media with the wt % amount of hydrolyzed soy concentrate and yeast extract concentrate as shown by the X axis. All FIG. 1 media also contained 1% by wt glucose.

Figure 2:
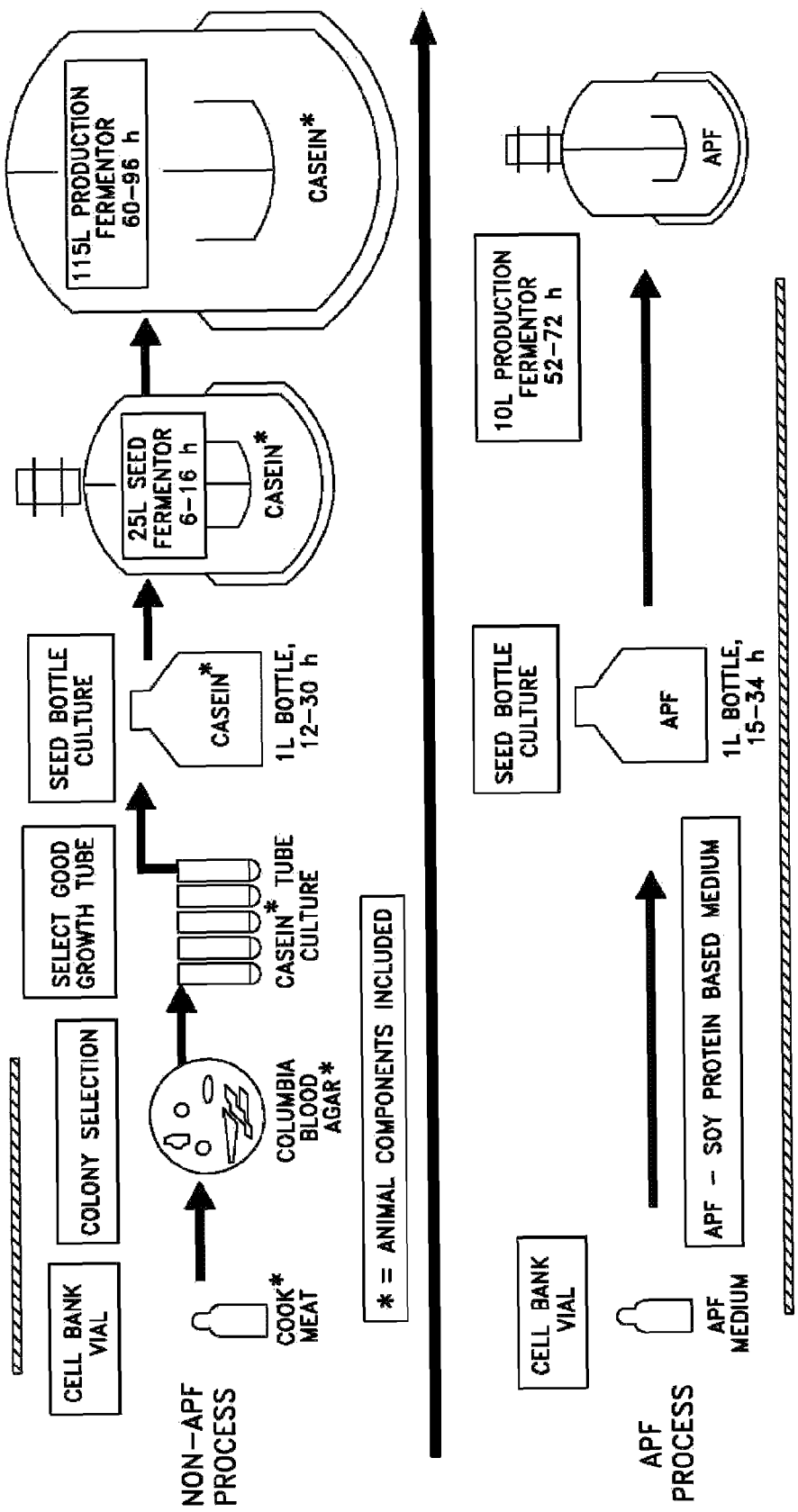

FIG. 2 is a summary flow chart comparing a non-APF process for obtaining a botulinum toxin (the top half of FIG. 1) with an APF process, within the scope of the present invention, for obtaining a botulinum toxin (the bottom half of FIG. 2), through the cell bank creation, culture and fermentation steps. FIG. 2 omits the harvest and purification steps.

Figure 3:
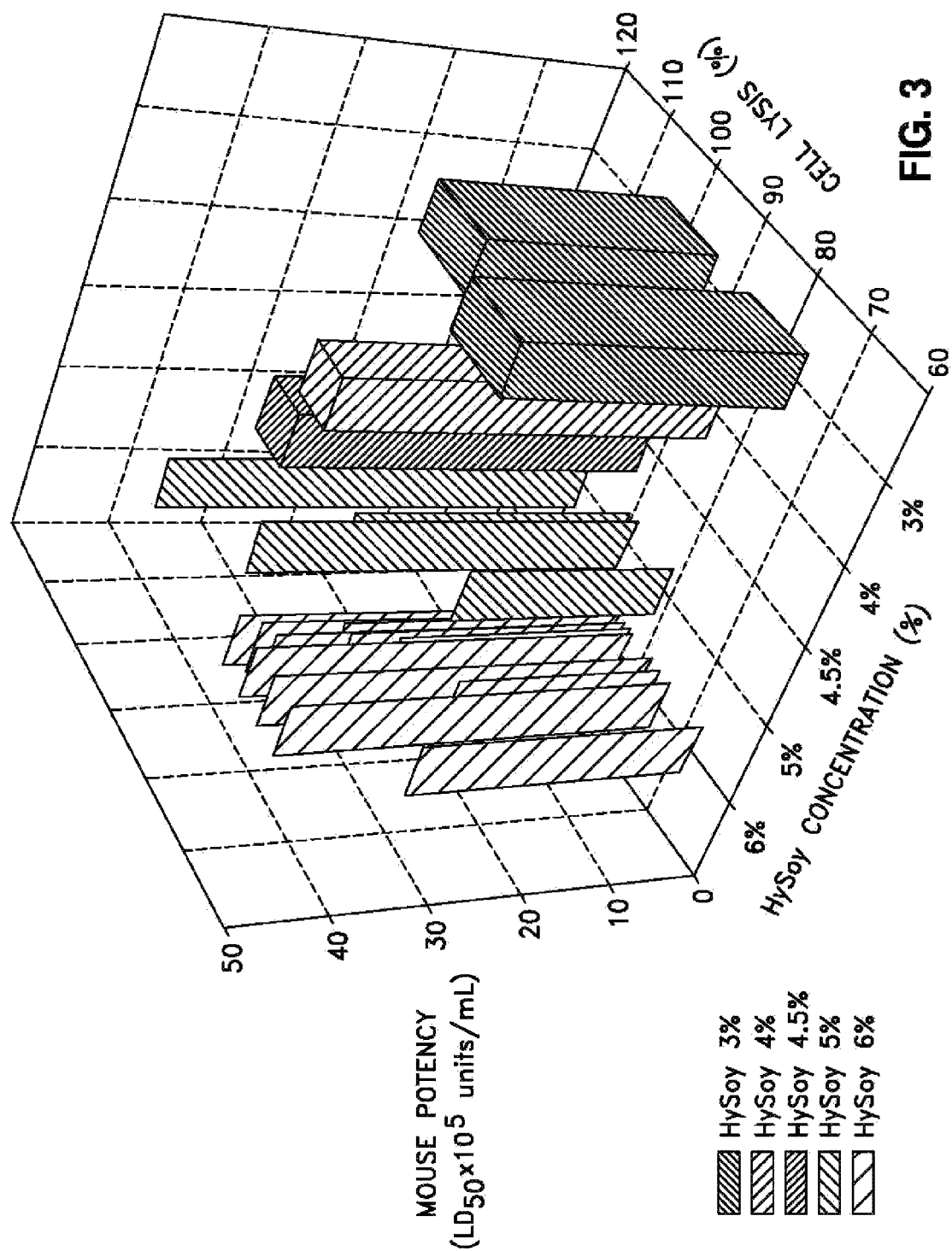

FIG. 3 is a graph comparing the effect of a soy protein concentration on a botulinum toxin type A complex production in an APF fermentation process, where the fermentation medium contained 1 wt % glucose and 1 wt % of a yeast extract. In FIG. 3 the X axis represents the weight percent concentration in the fermentation medium of a particular hydrolyzed soy protein (HySoy), the left side Y axis represents potency of the final purified botulinum toxin complex and the right side Y axis represents the percent of cell lysis completed, as determined by the equation:

$$\text{Cell Lysis } (\%) = \frac{OD_{600 \text{ max}} - OD_{600 \text{ endpoint}}}{OD_{600 \text{ max}}} \times 100$$

where $OD_{600\ max}$ corresponds to the optical density measured at 600 nm at the time of maximum growth, and $OD_{600\ endpoint}$ is at the time of fermentation harvest.

DESCRIPTION

The present invention is based upon the discovery of media and processes which are free or substantially free of an animal product or an animal byproduct useful for culture and fermentation of an organism (such as a *Clostridium botulinum* bacterium) capable of producing biologically active botulinum toxin. The botulinum toxin obtained can be used for making botulinum toxin active ingredient pharmaceutical compositions. Thus, growth media are disclosed herein which have significantly reduced levels of meat or dairy by-products and preferred media embodiments are substantially free of such animal products.

The present invention encompasses my surprising finding that animal-based products are not required in media for growth of *Clostridium botulinum*, and particularly that vegetable-based products can replace animal-based products typically employed in such media for the growth of *Clostridium botulinum*.

Media that are in current use for growth and fermentation of bacteria usually comprise one or more animal derived ingredients, such as coked meat. In accordance with my invention, preferred media for growth of *Clostridium botulinum* contain anima derived ingredients which comprise no more than about five to about ten percent of the total weight of the media. More preferably, media within the scope of my invention comprise no more than about one to less than about five percent of the total weight of the media of anima-derived products. Most preferably, all media and cultures used for the growth of *Clostridium botulinum* for the production of botulinum toxin are completely free of animal derived products. These media include but are not limited to media for small and large scale fermentation of *Clostridium botulinum*, media for growth of cultures of *Clostridium botulinum* used to inoculate the seed (first) media and fermentation (second) media, as well as and media used for long-term storage of cultures of *Clostridium botulinum* (e.g. stock cultures).

In certain preferred embodiments of my invention, the media for the growth of *Clostridium botulinum* and production of botulinum toxin can comprise soy based products to replace animal derived products. Alternately, instead of a soy based product there can be used debittered seed of *Lupinus campestris*. It is known the protein content of *L. campestris* seed is very similar to that of soybean. Preferably, these media include soybean or of *L. campestris* derived products that are hydrolyzed and that are soluble in water. However, insoluble soy or of *L. campestris* products can also be used in the present invention to replace animal products. Common animal derived products which can be substituted by soy or of *L. campestris* products include beef heart infusion (BHI), animal derived peptone products, such as Bacto-peptone, hydrolyzed caseins, and dairy by-products such as animal milk.

Preferably media containing soy-based or of *L. campestris* based products for the growth of *Clostridium botulinum* are similar to commonly used growth media containing animal derived products except that substantially all animal-derived products are replaced with vegetable-derived products. For example, soy based fermentation media can comprise a soy based product, a source of carbon such as glucose, salts such as NaCl and KCl, phosphate-containing ingredients such as $Na_2HPO_4$, $KH_2PO_4$, divalent cations such as iron and magnesium, iron powder, and amino acids such as L-cysteine and L-tyrosine. Media used to grow cultures of *Clostridium botulinum* for inoculation (i.e. the seed or first medium) of the fermentation (second) media preferably contain at least a soy based product, a source of salt such as NaCl, and a carbon source such as glucose.

The present invention provides a method for the growth of *Clostridium botulinum* that maximizes the production of a botulinum toxin using media that are substantially free of animal-derived products. Growth of *Clostridium botulinum* for production of botulinum toxin can take place by fermentation in media containing soy by-products that replace ingredients derived from animal by-products. The inoculant for the fermentation medium can be derived from a smaller scaled growth medium (a seed medium). Depending on the size and volume of the fermentation step, the number of successive growths in seed media to increase the biomass of the culture can vary. To grow a suitable amount of *Clostridium botulinum* for inoculating the fermentation medium, one step or multiple steps involving growth in a seed medium can be performed. For a method of growing *Clostridium botulinum* that is free of animal derived products, it is preferable that growth of *Clostridium botulinum* originates from a culture stored in non animal derived media. The stored culture, preferably lyophilized, is produced by growth in media containing proteins derived from soy and lacking animal by-products. Growth of *Clostridium botulinum* in a fermentation medium can take place by inoculation directly from a stored, lyophilized culture.

In a preferred embodiment of the present invention, growth of *Clostridium botulinum* proceeds in two phases-seed growth and fermentation. Both of these phases are carried out in anaerobic environments. The seed growth phase is generally used to "scale-up" the quantity of the microorganism from a stored culture. The purpose of the seed growth phase) is to increase the quantity of the microorganism available for fermentation. In addition, the seed growth phase allows relatively dormant microbes in stored cultures to rejuvenate and grow into actively growing cultures. Furthermore, the volume and quantity of viable microorganisms used to inoculate the fermentation culture can be controlled more accurately from an actively growing culture than from a stored culture. Thus, growth of a seed culture for inoculation of the fermentation medium is preferred. In addition, any number of consecutive steps involving growth in seed media to scale-up the quantity of *Clostridium botulinum* for inoculation of the fermentation medium can be used. It is noted that growth of *Clostridium botulinum* in the fermentation phase can proceed directly from the stored culture by direct inoculation.

In the fermentation phase, a portion of a seed medium or all of a seed medium containing *Clostridium botulinum* from the seed growth is used to inoculate a fermentation medium. Preferably, approximately 2-4% of a seed medium having *Clostridium botulinum* from the seed growth phase is used to inoculate the fermentation medium. Fermentation is used to produce the maximum amount of microbe in a large-scale anaerobic environment (Ljungdahl et al., *Manual of industrial microbiology and biotechnology* (1986), edited by Demain et al, American Society for Microbiology, Washington, D.C. page. 84).

A botulinum toxin can be isolated and purified using methods of protein purification well known to those of ordinary skill in the protein purification art. See e.g. Coligan et al. *Current Protocols in Protein Science*, Wiley & Sons; Ozutsumi et al. Appl. Environ. Microbiol. 49; 939-943:1985.

For production of botulinum toxin, cultures of *Clostridium botulinum* can be grown in a seed medium for inoculation of the fermentation medium. The number of successive steps involving growth in a seed medium can vary depending on the scale of the production of botulinum toxin in the fermentation phase. However, as previously discussed, growth in the fermentation phase may proceed directly from inoculation from a stored culture. Animal-based seed media generally are comprised of BHI, bacto-peptone, NaCl, and glucose for growth of *Clostridium botulinum*. As previously discussed, alternative seed media may be prepared in accordance with the present invention in which animal-based components are substituted with non-animal-based components. For example but without limitation, soy-based products can substitute for BHI and bacto-peptone in the seed medium for growth of *Clostridium botulinum* and production of botulinum toxin. Preferably, the soy-based product is soluble in water and comprises hydrolyzed soy, although cultures of *Clostridium botulinum* can grow in media containing insoluble soy. However, levels of growth and subsequent toxin production are greater in media derived from soluble soy products.

Any source of soy-based products may be used in accordance with the present invention. Preferably, the soy is hydrolyzed soy and the hydrolyzation has been carried out using non-animal enzymes. Sources of hydrolyzed soy are available from a variety of commercial vendors. These include but are not limited to Hy-Soy (Quest International), Soy peptone (Gibco) Bac-soytone (Difco), AMISOY (Quest), NZ soy (Quest), NZ soy BL4, NZ soy BL7, SE50M (DMV International Nutritionals, Fraser, N.Y.), and SE50MK (DMV). Most preferably, the source of hydrolyzed soy is Hy-Soy or SE50MK. Other potential sources of hydrolyzed soy are known.

Concentrations of Hy-Soy in the seed medium in accordance with the present invention range between 25-200 g/L. Preferably, the concentration of Hy-Soy in the seed medium ranges between 50-150 g/L. Most preferably the concentration of Hy-Soy in the seed medium is approximately 100 g/L. In addition, the concentration of NaCl ranges between 0.1-2.0 g/L. Preferably the concentration of NaCl ranges between 0.2-1.0 g/L. Most preferably, the concentration of NaCl in the seed medium is approximately 0.5 g/L. The concentration of glucose ranges between 0.1 g/L and 5.0 g/L. Preferably, the concentration of glucose ranges between 0.5-2.0 g/L. Most preferably, the concentration of glucose in the seed medium is approximately 1.0 g/L. It is also preferred but not necessary for the present invention that the glucose is sterilized by autoclaving together with the other components of the seed medium. The pH level of the seed medium prior to growth can be 7.5-8.5. For example, the pH of the seed medium prior to growth of *Clostridium botulinum* can be approximately 8.1.

Growth of *Clostridium botulinum* in the seed medium can proceed in one or more stages. Preferably, growth in the seed medium proceeds in two stages. In stage one, a culture of *Clostridium botulinum* is suspended in a quantity of seed medium and incubated at 34±1° C. for 24-48 hours in an anaerobic environment. Preferably, growth in stage one proceeds for approximately 48 hours. In stage two, a portion or all of the stage one medium containing *Clostridium botulinum* is used to inoculate a stage two seed medium for further growth. After inoculation, the stage two medium is incubated at 34±1° C. for approximately 1-4 days also in an anaerobic environment. Preferably, growth in the stage two seed medium proceeds for approximately 3 days. It is also preferable that growth in seed media in any stage does not result in cell lysis before inoculation of fermentation media with the final growth in seed medium.

Standard fermentation media containing animal by-products for the growth of *Clostridium botulinum* can be based on a recipe of Mueller and Miller (M M; J. Bacteriol. 67:271, 1954). The ingredients in MM media containing animal by-products include BHI and NZ-CaseTT. NZ-CaseTT is a commercially available source of peptides and amino acids which are derived from the enzymatic digestion of caseins, a group of proteins found in animal milk. The present invention demonstrates that non-animal based products may be substituted for BHI and NZ-CaseTT in fermentation media. For example but without limitation, soy-based products can replace the animal-based components of MM media used for fermentation of *Clostridium botulinum*. Preferably, the soy-based products are water-soluble and derived from hydrolyzed soy, although as previously discussed, insoluble soy products can also be used to practice the present invention.

Any source of soy-based products may be used in accordance with the present invention. Preferably, the hydrolyzed soy is obtained from Quest International (Sheffield) under the tradename, Hy-Soy or from DMV International Nutritionals (Fraser, N.Y.) under the tradename, SE50MK. Soluble soy products can be also obtained from a variety of sources including but not limited to Soy peptone (Gibco) Bac-soytone (Difco), AMISOY (Quest), NZ soy (Quest), NZ soy BL4, NZ soy BL7, and SE50MK (DMV International Nutritionals, Fraser, N.Y.).

In another preferred embodiment of the present invention, the medium used for fermentation of *Clostridium botulinum* is free of animal by-products and comprises hydrolyzed soy, glucose, NaCl, $Na_2HPO_4$, $MgSO_4 7H_2O$, $KH_2PO_4$, L-cysteine, L-tyrosine, and powdered iron. As disclosed for the seed medium, hydrolyzed soy can replace animal by-products in fermentation medium. These animal by-products include BHI and NZ-Case TT (enzymatically digested casein).

The concentration of Hy-Soy in the fermentation medium for production of botulinum toxin preferably ranges between approximately 10-100 g/L. Preferably, the concentration of Hy-Soy ranges between approximately 20-60 g/L. Most preferably, the concentration of Hy-Soy in the fermentation medium is approximately 35 g/L. For maximal production of botulinum toxin, particularly preferred concentrations of components in the fermentation medium are approximately 7.5 g/L, glucose; 5.0 g/L NaCl; 0.5 g/L $Na_2HPO_4$; 175 mg/L $KH_2PO_4$; 50 mg/L $MgSO_4 7H_2O$; 125 mg/L L-cysteine; and 125 mg/L L-tyrosine. The amount of powdered iron used can range from 50 mg/L to 2000 mg/L. Preferably, the amount of powdered iron ranges between approximately 100 mg/L and 1000 mg/L. Most preferably, the amount of powdered iron used in fermentation media ranges between approximately 200 mg/L and 600 mg/L.

For optimal levels of toxin production, the initial pH (before autoclaving) of the soy-based fermentation media ranges preferably between approximately 5.0 to 7.1. We found that pH control improves botulinum toxin recovery. Preferably the initial pH of the fermentation medium is about pH 7. As explained in Example 7, we have found that a high yield of stable botulinum toxin can be obtained if the pH is thereafter reduced to and maintained between pH 5-5.5. As described for the seed medium, the components of the fermentation medium, including glucose and iron, are preferably autoclaved together for sterilization.

Preferably, a portion of the second stage seed medium used for growth of *Clostridium botulinum* is used to inoculate the fermentation medium. Fermentation occurs in an anaerobic chamber at approximately 34±1° C. for approximately 7 to 9 days. Bacterial growth can be monitored by measuring the optical density (O.D.) of the medium. Fermentation preferably is stopped after cell lysis has proceeded for at least 48 hours as determined by growth measurement (optical density). As cells lyse, the O.D. of the medium decreases.

In a preferred embodiment of the present invention, cultures of *Clostridium botulinum* used for long-term storage of *Clostridium botulinum* and inoculation of the seed medium are grown and lyophilized in soy-milk prior to storage at 4° C. Cultures of *Clostridium botulinum* in animal milk lyophilized for storage can also be used for the production of botulinum toxin. However, to maintain media that are substantially free of animal by-products throughout the production of botulinum toxin, it is preferred that the initial culture of *Clostridium botulinum* be preserved in soy milk and not animal milk.

EXAMPLES

The following examples set forth specific methods encompassed by the present invention and are not intended to limit the scope of the invention. *Clostridium botulinum* cultures can be obtained from several sources, including List Laboratories, Campbell, Calif. In all the Examples below "*Clostridium botulinum*" means the Hall A (ATCC designation number 3502) strain of *Clostridium botulinum* type A.

Example 1

Preparation of an Animal Product Free Seed Medium for *Clostridium Botulinum*

A control seed medium can be prepared using the following ingredients for each one 1 liter of medium: NaCl (5 g), Bacto-peptone (10 g), glucose (10 g), BHI (to 1 liter), pH 8.1 (adjusted with 5 N NaOH).

A test (animal product free) seed medium can be prepared using the following ingredients for each one 1 liter of medium: NaCl (5 g), Soy-peptone (10 g), glucose (10 g), Hy-Soy (35 g/liter, to make up 1 liter of media fluid), pH 8.1 (adjusted with 5 N NaOH).

Example 2

Culturing *Clostridium Botulinum* in an Animal Product Free Seed Medium

A lyophilized culture of the *Clostridium botulinum* can be suspended in 1 ml of each of the control and test seed medium of Example 1, divided (each seed media) into two tubes of which each can contain 10 ml of the respective seed media, and then incubated at 34° C. for about 24-48 hours. One ml of culture can be then used to inoculate a 125 ml DeLong Bellco Culture Flask containing 40 ml of (the respective) seed media. The inoculated culture can be incubated at 33° C.±1° C. for 24 hours in a Coy Anaerobic Chamber (Coy Laboratory Products Inc., Grass Lake, Mich.).

Example 3

Preparation of an Animal Product Free Fermentation Media for *Clostridium Botulinum*

A basal fermentation medium can be prepared using the following ingredients for each two liters of medium: glucose (15 g), NaCl (10 g), $NaH_2PO_4$ (1 g), $KH_2PO_4$ (0.350 g), $MgSO_4 7H_2O$ (0.1 g), cysteine-HC (0.250 g), tyrosine-HCl (0.250 g), powdered iron (1 g), $ZnCl_2$ (0.250 g), and $MnCl_2$ (0.4 g).

A control fermentation medium can be prepared using the following ingredients for each two liters of medium prepared: BHI (500 ml; this corresponds to about 45.5 grams of dry weight beef heart infusion), NZ-CaseTT (30 g), and basal medium (to 2 liters), pH 6.8.

The basal fermentation medium can be prepared first and it's pH adjusted to pH 6.8. The beef heart infusion (BHI) BHI can then be prepared and it's pH adjusted to 0.8 with 5 N NaOH. The BHI can then be added to the basal medium. Next the NZ-CaseTT can be prepared. The NZ-Case TT is then added to the to basal medium to which the beef heart infusion has already been added, and dissolved by addition of HCl. The pH can then be adjusted to 6.8 with 5 N NaOH. This medium can then be separated into 8 ml portions into each of sixteen 100 mm test tubes, following by autoclaving for 25 minutes at 120° C.

A test fermentation medium (animal product free) can be prepared by substituting a test nitrogen source for the BHI present in the control fermentation medium. Suitable test fermentation medium nitrogen sources include: Hy-Soy (Quest), AMI-Soy (Quest), NZ-Soy (Quest), NZ-Soy BL4 (Quest), NZ-Soy BL7 (Quest), Sheftone D (Sheffield), SE50M (DMV), SE50 (DMV), SE %) MK (DMV), Soy Peptone (Gibco), Bacto-Soyton (Difco), Nutrisoy 2207 (ADM), Bakes Nutrisoy (ADM) Nutrisoy flour, Soybean meal, Bacto-Yeast Extract (Difco) Yeast Extract (Gibco), Hy-Yest 412 (Quest), Hy-Yest 441 (Quest), Hy-Yest 444 (Quest), Hy-Yest (455 (Quest) Bacto-Malt Extract (Difco), Corn Steep, and Proflo (Traders).

The test fermentation medium can be prepared as set forth above for a control fermentation medium except that BHI is excluded and the relevant nitrogen source can be first adjusted to pH 6.8 with 3 N HCl or with 5 N NaOH. The media can be allocated to in 8 ml portions to sixteen 100 mm test tubes, followed by autoclaving for 20-30 minutes at 120° C.

Example 4

Growth of *Clostridium Botulinum* in an Animal Product Free Fermentation Medium

A 40 µl portion of the test seed medium culture (animal product free) can be used to inoculate each 8 ml control or test fermentation medium aliquot in an 8 ml 16×100 mm test tube. The cultures can then be incubated at 33±1° C. for 24 hours. Tubes can then be incubated in an anaerobic chamber to allow for growth of the bacterium. Each medium assay can be performed in triplicate (i.e. can involve three independent inoculations of the same medium), and can also include a non-inoculated control, which can be used as the blank for the spectrophotometer). Growth (as determined by optical density, OD) can be measured every 24 hours with a Turner Spectrophotometer (Model 330) at 660 nm. Cultivation should be stopped after cell lysis has lasted for about 48 hours and botulinum toxin production can then be measured.

Additional experiments can be carried out with a Hy-Soy fermentation medium containing the following ingredients for each 500 ml of the medium: Hy-Soy (17.5 g), glucose (3.75 g); NaCl (2.5 g); $Na_2HPO_4$ (0.25 g), $MgSO_4 7H_2O$ (0.025 g), $KH_2PO_4$ (0.0875 g), L-cysteine (0.0625 g), L-tyrosine (0.0625 g), powdered iron (0.25 g), pH 6.8.

Example 5

Determination of Botulinum Toxin Production by *Clostridium Botulinum* Grown in an Animal Product Free Fermentation Medium The cultured cells of Example 4 can be centrifuged, and the pH of the supernatant then determined. The levels of botulinum toxin in a given sample can be measured by adding a standard antitoxin and measuring the elapsed time before flocculation. Both Kf (the time required for flocculation to occur, in minutes) and Lf (the limit of flocculation; equivalent to 1 international unit of standard antitoxin, as established by flocculation) can be determined. 4 ml of fermentation broth can be taken from each fermentation tube for a given culture, and can be combined together so that 12 ml total can be mixed in a 15 ml centrifuge tube. The tubes can be centrifuged at 5000 rpm (3400 g) for 30 min at 4° C. 1 ml aliquots of supernatant can be added to tubes containing 0.1-0.6 ml of standard botulinum toxin antiserum, and the tubes can be carefully shaken to mix their contents. The tubes can then be placed in a water bath at 45±1° C. and the initial time can be recorded. The tubes can be checked frequently, and the time at which flocculation began can be recorded as Kf. The concentration of toxin in the tube in which flocculation can be first initiated can be designated LfFF. The concentration of toxin in the tube in which flocculation can be initiated second can be designated LfF.

Parallel fermentation, growth and toxin production assays can be carried out for both of: (a) the control seed medium (used to inoculate the control fermentation medium) and the control fermentation medium, and; (2) the (animal product free) test seed medium (used to inoculate the test fermentation medium) and the (animal product free) test fermentation medium. Significantly, it can be determined that the fermentation of *Clostridium botulinum* in media free of animal products and inoculated from cultures also free of animal products (with soy-base products replacing the animal products) can result in an $Lf_{toxin}$ of approximately 50 or more. Minimally, $Lf_{toxin}$ equals approximately 10. Preferably the $Lf_{toxin}$ is at least 20. Most preferably the $Lf_{toxin}$ is greater than 50.

Additionally, it can be determined that various soy products support *Clostridium botulinum* growth in fermentation media lacking BHI. Thus soluble soy preparations can replace BHI for growth of *Clostridium botulinum*. The best concentration can be 12.5 or 25 g/L. Hy-Soy (Sheffield) can give the highest growth. Insoluble soy preparations can be less effective.

Furthermore, results can be obtained to show that Quest Hy-Soy, DMV SE50MK, and Quest NZ-Soy can be effective soy products in terms of their ability to replace BHI for *Clostridium botulinum* growth. The results can reveal that the soy products (such as Quest Hy-Soy, DMV SE50MK, and Quest NZ-Soy) that may be optimal for growth can also be effective at replacing BHI for toxin production. The best soy product for toxin production can be Quest Hy-Soy at 22.75 g/l. Higher concentrations of this product may produce better growth but not improve toxin production. Similar results can, it is proposed, be obtained with SE50MK, for which a higher concentration may generate increased growth, but not increase toxin production. NZ-Soy, on the other hand, may give higher growth and higher toxin production at its higher concentration.

Finally, it can be determined that soy products can effectively replace BHI as well as the NZ-CaseTT. Removal of NZ-CaseTT from soy-based media can reduce growth of about 2-4 fold. The best soy product for growth both in the presence and the absence of NZ-CaseTT can be SE50MK. HY-Soy can replace both BHI and NZ-CaseTT for toxin production. However, a longer fermentation cycle of 1 or 2 days may be necessary. HY-Soy could replace both BHI and NZ-CaseTT in media for toxin production. However, it can be determined that yeast extracts can be inhibitory to toxin production.

It can be determined that HY-Soy at 22.75 g/l may completely replace both BHI and HY-CaseTT for toxin production. Unlike the effect on growth where 56.88 g/l HY-Soy can be best, 34.13 g/l HY-Soy can be best for the toxin production phase.

Thus, it has surprisingly been determined if Hy-Soy or [Hy-Soy+Hy-Yest] can replace BHI and Bacto-peptone in media for seed growth of *Clostridium botulinum*. In addition, experiments can be designed to determine the optimum concentrations of components in seed media to produce the maximum levels of botulinum toxin production by the *Clostridium botulinum*. Toxin production by *Clostridium botulinum* grown in seed medium and fermentation medium that is free of BHI and NZ-CaseTT can reach or exceed levels attained in media containing BHI and NZ-CaseTT.

It can be determined that the optimum concentrations of Hy-Soy or [Hy-Soy+Hy-Yest] for growth in the seed medium. Experiments can confirm that Hy-Soy can replace BHI and Bacto-peptone as the nitrogen source in seed medium for growth of *Clostridium botulinum* and for production of botulinum toxin in the subsequent fermentation phase. Also, Hy-Soy as nitrogen source in the seed medium, as compared to Hy-Soy plus Hy-Yest, can produce higher levels of botulinum toxin in the subsequent fermentation step. The concentrations of Hy-Soy in seed medium that produce the best levels of toxin range from approximately 62.5 g/L to 100 g/L.

Additional experiments can be designed to determine the optimum concentrations of Hy-Soy in the seed medium for the maximum production of botulinum toxin by *Clostridium botulinum* by fermentation. Thus, 30 g, 50 g, 75 g and 100 g of Hy-Soy in the seed medium can all resulted in production of botulinum toxin by fermentation of *Clostridium botulinum* and this is comparable or exceeds levels of botulinum toxin made in seed medium containing BHI and Bacto-peptone as a nitrogen source.

It can be found that a concentration of 100 g/L Hy-Soy in the seed medium resulted in the highest levels of toxin production in the subsequent fermentation step. In addition, the data indicate that seed step-1 of Hy-Soy seed medium produced greater growth after 48 hours than after 24 hours.

Example 6

Non-APF Process for Obtaining a Botulinum Toxin

A Clostridial toxin was obtained by fermentation of a *Clostridium botulinum* bacterium. Thus, a modified Schantz (non-APF) process was carried out to obtain highly potent and highly purified *Clostridium botulinum* toxin (i.e. bulk toxin) as follows. A modified Schantz (non-APF) process can provide a high yield of botulinum toxin. Both Schantz and modified Schantz processes use casein in all the fermentation media.

Stock Culture Preparation

Various Clostridial bacteria are available from the American Type Culture Collection (ATCC), Manassas, Va. Alternately, a *Clostridium botulinum* cell bank vial can be prepared by isolating *Clostridium botulinum* from various sources, including soil or by deep sampling (at anaerobic or at quasi-anaerobic locations) of putrefying animal carcasses. Commonly, *Clostridium botulinum* can be obtained from a sample of a physiological fluid (i.e. a wound swap from a patient with wound botulism) of a patient diagnosed with botulism. The top half of FIG. 1 summarizes the non-APF process used for preparation of a cell bank vial, and for the culture and fermentation of a botulinum toxin.

The *Clostridium botulinum* obtained from a natural or patient source is cultured on blood agar plates, followed by inoculation of high growth colonies into a cell bank vial medium. The cell bank vial medium used for *Clostridium botulinum* was a cooked meat medium which contains chopped fresh beef. Actively growing cultures were mixed with glycerol to prepare a cell bank vial (i.e. a stock culture) of the *Clostridium botulinum* bacterium which was frozen for later use.

Seed Cultivations

A *Clostridium botulinum* cell bank vial was thawed at room temperature, followed by four cultivation steps. (1) To select colonies with a suitable morphology, aliquots from the thawed cell bank vial were cultivated by streaking the bacterium on pre-reduced Columbia blood agar plates and anaerobically incubating for 30-48 hours at 34° C.±1°. (2) Selected colonies were then inoculated into test tubes containing a casein growth medium for 6-12 hours at 34° C. The contents of the tube with the most rapid growth and highest density (growth selection step) were then further cultivated through two step-up anaerobic incubations: (3) a first 12-30 hour incubation at 34° C. in a one liter seed cultivation bottle, followed by (4) a second cultivation in a 25 liter seed fermenter containing a casein growth medium for 6-16 hours at 35° C. These two step-up cultivations were carried out in a nutritive media containing 2% casein hydrolysate (a casein [milk protein] digest), 1% yeast extract and 1% glucose (dextrose) in water at pH 7.3.

Fermentation

The step-up cultivations were followed by a further incubation for 60-96 hours at 35° C. in a commercial scale (i.e. 115 liter) fermenter in a casein containing medium under a controlled anaerobic atmosphere. Growth of the bacterium is usually complete after 24 to 36 hours, and during the 60-96 hour fermentation most of the cells undergo lysis and release botulinum toxin. Control of the fermentation medium pH is not required in a Schantz or modified Schantz process. It is believed that toxin is liberated by cell lysis is activated by proteases present in the culture broth. Optionally, a filtration of this culture medium using a single layer depth filter to remove gross impurities (i.e. whole and ruptured cells) can be prepared to obtain a clear solution referred to a clarified culture.

Harvest

Harvest of toxin can be accomplished by lowering the pH to 3.5 with sulfuric acid to precipitate the raw toxin at 20° C. The raw toxin was then concentrated by ultramicrofiltration followed by diafiltration.

Purification

The harvested crude toxin was then transferred to a digestion vessel and stabilized by addition of the protease inhibitor benzamidine hydrochloride. DNase and RNase were added to digest nucleic acids. The toxin containing material was subjected to UF/DF and three precipitation steps (cold ethanol, hydrochloric acid and ammonia sulfate precipitations). The purified botulinum neurotoxin complex (bulk toxin) was stored as a suspension in a sodium phosphate/ammonium sulphate buffer at 2-8 degrees C.

The resulting bulk toxin was a high quality crystalline 900 kD botulinum toxin type A complex made from the Hall A strain of *Clostridium botulinum* with a specific potency of $\geq 3 \times 10^7$ U/mg, an $A_{260}/A_{278}$ of less than 0.60 and a distinct pattern of banding on gel electrophoresis, and suitable for use for the compounding of a botulinum toxin pharmaceutical composition.

Compounding can encompass a many fold dilution of the bulk toxin, mixing with one or more excipients (such as albumin and sodium chloride) to thereby form a toxin composition, and preparation of a storage and shipment stable form of the toxin composition, as by lyophilizing, freeze drying or vacuum drying the composition.

The purified botulinum toxin complex obtained from a Schantz or modified Schantz process can be eluted from an ion exchange column in a pH 7-8 buffer to disassociate the non toxin complex proteins from the botulinum toxin molecule, thereby providing (depending upon the type of *Clostridium botulinum* bacterium fermented) pure botulinum toxin type A with an approximately 150 kD molecular weight, and a specific potency of $1-2 \times 10^8$ LD$_{50}$ U/mg or greater; or purified botulinum toxin type B with an approximately 156 kD molecular weight and a specific potency of $1-2 \times 10^8$ LD$_{50}$ U/mg or greater, or purified botulinum toxin type F with an approximately 155 kD molecular weight and a specific potency of $1-2 \times 10^7$ LD$_{50}$ U/mg or greater.

Example 7

APF Media and Process for Obtaining a Botulinum Toxin

This example sets forth an APF process carried out to obtain highly potent and highly purified *Clostridium botulinum* toxin type A (i.e. bulk toxin). The process can be used with other botulinum toxin serotypes.

Stock Culture Preparation

As set forth in Example 6, *Clostridial botulinum* can be obtained from the ATCC, from various sources in nature or from a botulism patient. The bottom half of FIG. 1 summarizes the APF process used for preparation of a cell bank vial, and for the culture and fermentation of a botulinum toxin. APF cell bank vials were prepared by culturing *Clostridium botulinum* on plant agar plates. The plant agar plates were made by mixing the soy derivative HySoy (Quest) with a yeast extract and glucose in a 3:1:1 (weight percent) ratio with agar and allowing setting. Other commercially available APF agar plates or dehydrated powder for making the plates were also found to be suitable. Selected high growth colonies were then inoculated into an APF cell bank vial medium. The APF cell bank vial medium used comprised hydrolyzed soy protein, yeast extract (no animal product was used in either the cultivation of the yeast or in the process for preparation of the yeast extract made therefrom) and glucose in the same 3:1:1 ratio. Other nutrient ratios (i.e. 6:1:1, 6:0:1 and 6:3:1 were also found to be suitable). The hydrolyzed soy (HySoy) and yeast extract (HyYest) concentrates used were obtained from Quest International. The *Clostridium botulinum* culture in the APF medium was combined with glycerol, aliquoted to cryovials and frozen for later use. The APF media developed can be used to store the *Clostridial botulinum* bacteria for a period of one year or longer without loss of viability. These frozen culture and glycerol mixtures in cryovials are the APF cell bank vials.

Seed Cultivations

A/n APF cell bank vial was thawed at room temperature, followed by a single cultivation step: a one liter seed culture bottle was then inoculated directly (i.e. without an intervening blood agar culture or tube growth steps) with the APF cell bank vial contents using the same APF medium (the APF cell bank vial [storage] medium can be different from the APF fermentation [growth] medium) and maintained at 35° C. for 15 to 24 hours, with an initial medium pH of 7.0 in an anaerobic (nitrogen) atmosphere.

Fermentation

Next the seed bottle culture was transferred to a commercial scale 10 liter production fermenter containing the APF medium (hydrolyzed soy protein, yeast extract and 1% glucose) maintained at 35° C. for 52-72 hours, with an initial medium pH of 7.0, in an anaerobic (nitrogen) atmosphere. Approximately 15 hours after commencement of the fermentation (the culture pH has naturally decreased to below 6.0), a pH control program at range of pH 5.0-5.5 is initiated by adding HCl to the culture. It was found that it was necessary to control the pH of the APF fermentation medium within the narrow range in order to obtain an acceptable yield of active botulinum toxin. Thus, it was found that this pH control to between pH 5.0-5.5 substantially prevented degradation and loss of potency of the botulinum toxin. It is believed that during the fermentation most of the cells undergo lysis and release botulinum toxin and that toxin liberated by cell lysis is activated by proteases present in the culture broth. Filtration of this culture medium using a single layer depth filter removes gross impurities (i.e. whole and ruptured cells) and results in a clear solution referred to a clarified culture.

Harvest

Harvest of botulinum toxin can then proceed as in Example 6 (i.e. sulfuric acid precipitation, followed by concentrated by microfiltration followed by diafiltration).

Purification

Purification of the toxin can then proceed as set forth in Example 6: i.e. addition of benzamidine hydrochloride, and DNase and RNase, sulfuric acid precipitation, cold ethanol precipitation, phosphate buffer extraction, hydrochloric acid precipitation, phosphate buffer extraction and bulk toxin storage.

As an alternative to the Example 6 harvest and purification process, a column chromatography process can be carried out.

The resulting bulk toxin is a high quality crystalline 900 kD botulinum toxin type A complex made from the Hall A strain of *Clostridium botulinum* with a specific potency of $\geq 3 \times 10^7$ U/mg, an $A_{260}/A_{278}$ of less than 0.60 and a distinct pattern of banding on gel electrophoresis, and suitable for use for the compounding of a botulinum toxin pharmaceutical composition. Thus, this APF process for a botulinum toxin can generate high quality toxin.

The purified botulinum toxin complex obtained from an APF process can be passed through and eluted from an ion exchange column in a pH 7-8 buffer to disassociate the non toxin complex proteins from the botulinum toxin molecule, thereby providing (depending upon the serotype of *Clostridium botulinum* bacterium fermented) botulinum toxin with an approximately 150 kD molecular weight, and a specific potency of $1-2 \times 10^8$ $LD_{50}$ U/mg or greater; or purified botulinum toxin type B with an approximately 156 kD molecular weight and a specific potency of $1-2 \times 10^8$ $LD_{50}$ U/mg or greater, or purified botulinum toxin type F with an approximately 155 kD molecular weight and a specific potency of $1-2 \times 10^7$ $LD_{50}$ U/mg or greater. For example, by use of our APF medium we were able to obtain a botulinum toxin type A complex with a specific potency of $1.02 \times 10^8$ $LD_{50}$ U/mg of the botulinum toxin.

In this Example 7 APF media with either 1% by wt or 2% by wt glucose were used (note that 1% glucose means 1 g of glucose per 100 ml of the culture medium and 2% glucose means 2 g of glucose were present for each 100 ml of the culture medium) and it was determined that maximal bacterium growth (as determined by peak optical density [optical density was measured at 600 nm] of the culture) occurred after about 20 hours of fermentation in the 1% glucose APF medium vs after about 40 hours of fermentation in the 2% glucose APF medium, but that the peak optical densities did not differ significantly as the glucose content of the media was so varied. It was believed that cell autolysis and toxin release resulted in a maximal amount of active botulinum toxin in the 1% glucose APF media (as determined by a SNAP-25 assay for active toxin) after about 55 hours of fermentation, but that with the 2% glucose APF media the amount of active botulinum toxin present in the medium at a later time (as determined by a SNAP-25 assay for active toxin) and was still increasing after 65 hours of fermentation. Thus, a more rapid release of botulinum toxin occurred with use of the lower (1%) glucose APF medium amount present, indicating that a more efficient toxin production process (i.e. more amount of toxin obtained per unit of time) can be carried out with use of the lower (1%) glucose APF medium.

As shown by FIG. 1, it was also determined that optimal parameters for production of botulinum toxin in an APF medium were the combination of the following parameters: (1) about 6% by weight of a hydrolyzed soy concentration ("HySoy Conc." in FIG. 1) in the APF fermentation medium. 6% soy means 6 g of the soy protein per 100 ml of the culture medium; (2) 0% to 3% yeast extract concentrate ("YE Conc." in FIG. 1) in the APF fermentation medium; (3) 50-72 hours of fermentation at a temperature of 33-35° C. under anaerobic (nitrogen atmosphere) conditions; (4) pH of the fermentation medium maintained between about pH 5.0 to 5.5 throughout the fermentation period after the initial cell growth, and (5) 1 wt % glucose in the APF fermentation medium.

Thus, as shown by FIG. 1 as more protein is present in the APF medium (as the total amount of HySoy and YE) the pH of the medium tends to increase with resulting lower toxin stability and that when the pH was lowered with the same total protein nutrient content in the medium, toxin production yield increased dramatically. In the non-APF process the total protein content is lower so that pH does not tend to rise and therefore there is no elevated pH to have a deleterious effect on toxin production. FIG. 1 shows that there was consistently more activity (as determined by the MLD50 and SNAP-25 assays) when the pH of the medium was controlled to within a narrow range of about 5.3 to 5.5. FIG. 1 also shows that the highest toxin yield (as determined by the SNAP 25 assay) was obtained with a medium which comprised 6% hydrolyzed soy and 1% yeast extract. FIG. 3 shows that when the yeast and glucose nutrients were both held at 1 wt %, that cell lysis between 68-100% and potency up to about 38 MLD units× $10^5$/mL of toxin was obtained as the soy protein was varied from 1 to 6% wt.

The SNAP-25 assay used was an ELISA based method to measure SNAP-25 proteolytic activity of the botulinum toxin. SNAP-25 is an abbreviation for synaptosome associated protein of 25 kDa molecular weight. SNAP-25 is a 206 amino acid plasma membrane protein involved in neuronal exocytosis. The assay is based on the method disclosed in Ekong T., et al., *Recombinant SNAP-25 is an effective substrate for Clostridium botulinum type A toxin endopeptidase activity in vitro*, Microbiology (1997), vol 143, pages 3337-3347. The assay uses a truncated SNAP-25 protein (the 206 amino acid residue peptide) bound to polystyrene 96 well microtiter plates and a monoclonal antibody that recognizes the cleaved product (a 197 amino acid residue peptide) which is made by enzymatic hydrolysis between amino acids 197 and 198 of the SNAP-25 by reduced botulinum toxin type A. The monoclonal antibody bound to the cleaved product is then detected with a secondary antibody (goat anti-mouse IgG conjugated to horseradish peroxidase [HRP]), which produces a color change in the presence of a chromogenic substrate (TMB).

The MLD50 (mouse 50% lethal dose) assay is a method for measuring the potency of a botulinum toxin by intraperitoneal injection of the botulinum toxin into female mice (about four weeks old) weighing 17-22 grams each at the start of the assay. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in saline. The death rates over the ensuing 72 hours for each dilution are recorded. The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin.

Significantly, our APF process differs from the Example 6 non-APF process, by at least: (1) replacing the cell bank vial cooked meat medium with an APF medium; (2) eliminating the blood agar colony selection step; (3) eliminating the subsequent casein medium based tube growth step, and; (4) replacing the non-APF fermentation media with APF media throughout.

FIG. 2 presents a summary of the differences between an industrial scale (non-APF) Schantz process (Example 6) and the industrial scale APF process of Example 7, through the cell bank creation, culture and fermentation steps. FIG. 2 omits the harvest and purification steps We also found that APF media can be used to select for *Clostridium botulinum* bacteria. Thus, concurrent practice of the Examples 6 and 7 initial culture steps permits isolation and growth of a *Clostridium botulinum* bacteria with characteristics conducive to growth and production of botulinum toxins in or on an APF medium. The transfer of *Clostridium botulinum* culture from a non-APF medium to an APF medium enriches for and selects for bacteria that can either adapt to the new environment or through selective die off of bacteria that cannot grow and produce in the new environment.

Various publications, patents and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of animal product free processes are within the scope of the present invention.

Accordingly, the spirit and scope of the following claims should not be limited to the descriptions of the preferred embodiments set forth above.

We claim:

1. A medium for culturing and/or for fermenting a *Clostridium botulinum* bacterium, wherein the medium is essentially free of an animal protein product and the medium comprises: (a) between about 4-8% by weight of a soy protein product; (b) between about 0-3% by weight of a yeast extract, and; (c) between about 1-2% by weight glucose, and wherein the medium comprises a *Clostridium botulinum* bacterium.

2. The medium of claim 1, further comprising a biologically active botulinum toxin.

3. The medium of claim 2, wherein the biologically active botulinum toxin is botulinum toxin type A.

4. An essentially animal protein free medium for culturing or fermenting a *Clostridium* bacterium, comprising:
a soy protein product, a yeast extract and glucose in about a 3-6:0-3:1 weight % ratio, respectively, and wherein the medium comprises a *Clostridium botulinum* bacterium.

5. The medium of claim 4, wherein the medium has an initial pH of 7 and is maintained in an anaerobic atmosphere.

6. The medium of claim 4, wherein the *Clostridium botulinum* bacterium had been maintained in a frozen state in the medium with glycerol.

7. The medium of claim 6, wherein the medium is subjected to a pH control program while fermentation of a culture of *Clostridium botulinum* bacterium proceeds until most of the *clostridium* bacteria undergo lysis.

8. The medium of claim 7, wherein the pH control program maintains the medium between about pH 5.0-5.5.

9. The medium of claim 8, wherein maintenance of pH between about pH 5.0-5.5 is provided by addition of acid to the medium.

10. The medium of claim 7, wherein said medium is subjected to filtration such that gross impurities are removed from the medium.

11. The medium of claim 10, wherein the medium further comprises sulfuric acid.

12. The medium of claim 6, wherein the medium is maintained in an anaerobic environment.

13. The medium of claim 4, further comprising a biologically active botulinum toxin.

14. The medium of claim 13, wherein the biologically active botulinum toxin is botulinum toxin type A.

* * * * *